United States Patent [19]

Nakazawa et al.

[11] Patent Number: 5,178,744
[45] Date of Patent: Jan. 12, 1993

[54] OXYGEN SENSOR DEVICE

[75] Inventors: Mitsuhiro Nakazawa, Sakura; Kousei Ishibashi, Chiba; Hideo Yamamoto, Tokyo; Akiyoshi Asada, Toikyo; Takafumi Kashima, Tokyo; Katsuaki Nakamura, Kimitsu, all of Japan

[73] Assignee: Fujikura Ltd., Tokyo, Japan

[21] Appl. No.: 747,411

[22] Filed: Aug. 19, 1991

Related U.S. Application Data

[63] Continuation of Ser. No. 373,974, Jun. 30, 1989.

[30] Foreign Application Priority Data

| Oct. 31, 1988 | [JP] | Japan | 63-275719 |
| Dec. 29, 1988 | [JP] | Japan | 63-333477 |
| Dec. 29, 1988 | [JP] | Japan | 63-333481 |
| Feb. 28, 1989 | [JP] | Japan | 1-21314[U] |

[51] Int. Cl.$^5$ ........................... G01N 27/417
[52] U.S. Cl. ........................... 204/425; 204/424; 204/426; 204/427; 204/429
[58] Field of Search ........................... 204/421–429

[56] References Cited

U.S. PATENT DOCUMENTS

| Re. 28,792 | 4/1976 | Ruka et al. | 204/1 |
| 3,691,023 | 9/1972 | Ruka et al. | 204/1 |
| 3,768,259 | 10/1973 | Carnahan et al. | 60/276 |
| 3,787,308 | 1/1974 | Malaspina et al. | 204/195 |
| 3,907,657 | 9/1975 | Heinje et al. | 204/195 |
| 4,334,974 | 6/1982 | Muller et al. | 204/426 |
| 4,502,939 | 3/1985 | Holfelder et al. | 204/427 |
| 4,571,285 | 2/1986 | Nakazawa et al. | 204/1 |
| 4,574,627 | 3/1986 | Sakurai et al. | 204/426 |
| 4,762,605 | 8/1988 | Tanaka et al. | 204/406 |

FOREIGN PATENT DOCUMENTS

| 61-34456 | 2/1986 | Japan . |
| 63-41762 | 3/1988 | Japan . |

*Primary Examiner*—T. Tung
*Attorney, Agent, or Firm*—Armstrong, Westerman, Hattori, McLeland & Naughton

[57] ABSTRACT

An oxygen sensor device is disclosed having a glass dome fluid-tightly connected at its circumferential base edge to one surface of an oxygen conductive solid electrolyte plate to form a diffusion chamber defined by the glass dome and the solid electrolyte plate. The diffusion chamber may be vacant, or may have a porous inorganic material packing layer fixedly disposed in the entire space thereof. Alternatively, the diffusion chamber may have a porous inorganic material semi-packing layer fixedly disposed in an upper portion thereof remote from the electrolyte plate, while leaving vacant the remainder of the chamber. The oxygen sensor device is advantageous from the viewpoints of miniaturization, power consumption saving and reliability.

17 Claims, 9 Drawing Sheets

OXYGEN SENSOR DEVICE

This application is a continuation of application Ser. No. 07/373,974, filed Jun. 30, 1989.

BACKGROUND OF THE INVENTION

1. Field Of The Invention

The present invention relates to an oxygen sensor device. More particularly, the present invention is concerned with an oxygen sensor device having a glass dome fluid-tightly connected at its circumferential base edge to one surface of an oxygen conductive solid electrolyte plate to form a diffusion chamber defined by the glass dome and the solid electrolyte plate. The oxygen sensor device is advantageous from the viewpoints of miniaturization, power consumption saving and reliability. The advantageous oxygen sensor device can be efficiently produced by a novel method, in which a burnable material layer, a porous antifire material layer or a combination of a burnable material layer and a porous antifire material layer is formed on an oxygen conductive solid electrolyte plate and a powdery glass-containing pasty material is coated thereon, followed by firing. By virtue of the novel method, it is possible to perform continuous mass production of the oxygen sensor device at low cost, with the minimized occurrence of defectives.

2. Discussion Of Related Art

Oxygen determining devices are required when human beings must work in confined spaces, such as mines, tanks, etc. Oxygen determining devices are also requisite in extremely diversified fields, such as space ships and capsules, submarines for naval and civilian use, medical treatment, food pack inspection as well as combustion control and other environmental studies. Although several types of oxygen sensor devices have been proposed, there is still a strong demand for a small reliable oxygen sensor device.

A representative form of the conventional oxygen sensor device is shown in FIG. 1. The device comprises diffusion housing 104, oxygen conductive plate 101 of solid electrolyte hermetically bonded at its one surface to diffusion housing 104 by sealing glass 107, and a pair of circular electrode layers 102A and 102B secured to the opposite sides of conductive plate 101, respectively. Electrodes 102A and 102B are connected to a DC power source. For example, the oxygen conductive plate 101 comprises a solid solution containing $ZrO_2$, $Y_2O_3$, MgO and CaO. Each of electrode layers 102A and 102B is porous and is made of, for example, platinum. Diffusion housing 104 has orifice 105 (gas inlet means) of a small diameter formed through the wall of the housing. The diffusion of oxygen from the monitored gas environment through gas inlet means 105 into chamber 103 of diffusion housing 104 is effected by the application of a DC potential from a power source across two electrodes 102A and 102B to pump the oxygen present in chamber 103 through oxygen conductive plate 101. As the potential across two electrodes 102A and 102B is increased, electrical current flowing through two electrodes 102A and 102B is changed. The current limited by the oxygen diffusion becomes stable so that a stable diffusion limited current value is obtained. The diffusion limited current value is proportional to the concentration of oxygen in the monitored gas environment, and therefore the oxygen concentration can be detected by measuring the diffusion limited current value through a current meter (see, for example, U.S. Pat. No. 4,571,285).

In another conventional oxygen sensor device, the diffusion housing is made of an open-cell porous structure, with the gas inlet means omitted. With this construction, the oxygen diffuses into the chamber defined by the housing and the electrolyte plate through the pores of the housing.

Generally, it is desired that the oxygen sensor device have a small size, because, with the small size, it is easy to heat up the device and perform temperature control at the time of oxygen determination, and the oxygen sensor device can be applied to oxygen determination even when the space at the oxygen determination site is limited. In manufacturing the above-mentioned conventional oxygen sensor devices, miniaturization of the device to a size of some millimeters is accompanied by difficulties in the fabrication and assembly of components, such as housing and solid electrolyte. For example, diffusion housing 104 is made of a hard material, such as that prepared by firing a ceramic. It is very difficult to rework such a hard material into a diffusion housing of small size which has complicated configuration. Further, it is also very difficult to fluid-tightly connect such a small diffusion housing to a solid electrolyte plate. In particular, the connection of the diffusion housing to the solid electrolyte plate is carried out by applying sealing glass and then melting the glass in a high-temperature oven. However, this operation is likely to cause positional displacement, thereby leading to a high ratio of defectives. Because of the above-mentioned difficulties, the conventional oxygen sensor devices is likely to lack reliability in quality, and the productivity of the devices is disadvantageously low.

U.S. Pat. No. 4,762,605 discloses an improved method for manufacturing an oxygen sensor device In the improved method, a green sheet is used. The terminology "green sheet" used herein means a flexible plate or sheet comprising ceramic particles bound with a plasticizer, such as that prepared by first blending together a powdery ceramic, an organic resin plasticizer, e.g., polyethylene glycol, and a solvent, e.g., water and an alcohol, secondly extruding the resultant blend through rolls or a slit into a sheet and thirdly evaporating the solvent at a temperature, e.g. 100° to 500° C. A representative mode of this improved method is described below. First, a layer of a burnable resin material is disposed on the cathode side of an oxygen conductive solid electrolyte plate sandwiched between a porous cathode and a porous anode. Secondly, a pin-shaped protrusion made of the same resin material or of a hard plastic or an aluminum filament each having a low melting temperature is embedded in the layer of the burnable resin material. Thirdly, the above-mentioned green sheet is disposed on the layer of the burnable resin material. At this time, the protrusion passes through the layer. Finally, firing is performed. As a result, the plasticizer, the resin material and 5 the hard plastic are burnt, and the aluminum filament is melted off. Thus, an oxygen sensor device comprising an oxygen conductive solid electrolyte plate sandwiched between a porous cathode and a porous anode and a ceramic diffusion housing connected at its circumferential base edge to the cathode side of the solid electrolyte plate, is obtained, having a similar structure to that of FIG. 1. In this method, the firing must be performed at a temperature as high as about 1600° C. This high temperature firing is likely to damage the pore structure of the cathode and anode, because the pore structure of each electrode is adversely affected at a temperature of higher than 1000° C. Also, the temperature as high as about 1600° C. is likely to cause deformation of the electrolyte plate. Therefore, it is very difficult to produce continuously such a type of oxygen sensor with uniform, excellent quality on a commercial scale.

SUMMARY OF THE INVENTION

The present inventors have made extensive and intensive studies with a view toward obviating the drawbacks of the prior art. As a result, the inventors have unexpectedly found that an oxygen sensor device which is desirable from the viewpoints of miniaturization, power consumption saving and reliability can be realized by a structure in which a glass dome is fluid-tightly connected at its circumferential base edge to one surface of an oxygen conductive solid electrolyte plate. In view of the general knowledge with respect to the properties of glasses, it is surprising that an oxygen sensor device, the housing of which is constructed of a glass dome, can endure heat hysteresis caused by the change of temperature in the range of from room temperature (at the time the sensor is not working) to about 500° C or higher (at the time the sensor is working). Moreover, the inventors have found that the desirable oxygen sensor device can be efficiently produced by first forming a burnable material layer, a porous antifire material layer or a composite layer of burnable material and porous antifire material on an electrode-carrying oxygen conductive solid electrolyte, and coating thereon, e.g., by screen printing, a powdery glass-containing pasty material, followed by firing at a relatively low temperature, e.g. 600° to 1000° C. It is also surprising that the presence of the porous antifire material layer in the chamber defined by the glass dome and the solid electrolyte does not adversely affect the diffusion of gas and the sensitivity of the ultimate oxygen sensor device. Based on these novel findings, the present invention has been completed.

Accordingly, it is an object of the present invention to provide a novel oxygen sensor device which is desirable from the viewpoints of miniaturization, power consumption saving and reliability.

The foregoing and other objects, features and advantages of the present invention will be apparent from the following detailed description and appended claims taken in connection with the accompanying drawings.

BRIEF DESCRIPTION OF THE DRAWINGS

In the accompanying drawings:

FIGS. 7(A) to 7(C) are diagrammatic cross-sectional views to be used for explaining a method for producing an oxygen sensor device of the present invention in which a porous inorganic material is fixedly disposed in the diffusion chamber;

FIGS. 11(B) is a diagrammatic cross-sectional view of the oxygen sensor device of the present invention produced by the method shown in FIG. 11(A);

In FIGS. 1 through 16, like parts or portions are designated by like numerals or characters.

DETAILED DESCRIPTION OF THE INVENTION

Essentially, according to the present invention, there is provided an oxygen sensor device comprising:

an oxygen conductive solid electrolyte plate;

a first electrode and a second electrode respectively disposed on the upper surface and the lower surface of said solid electrolyte plate;

a first electric lead means and a second electric lead means respectively for connecting said first and second electrodes to power source means; and a glass dome fluid-tightly connected at its circumferential base edge to the upper surface of said solid electrolyte plate to provide at least one diffusion chamber defined by said glass dome and said solid electrolyte plate, said glass dome comprising at least one glass layer;

said glass dome or said solid electrolyte plate having a gas inlet means for diffusing ambient gas into said diffusion chamber;

said oxygen sensor device being operable by energizing said solid electrolyte plate, so that oxygen is pumped out of said diffusion chamber through said solid electrolyte plate to flow electric current across said first and second electrodes, said electric current being indicative of the partial pressure of the oxygen in the ambient gas.

The present invention will now be described in more detail with reference to the accompanying drawings.

In the oxygen sensor device of the present invention, the diffusion chamber defined by the glass dome and the solid electrolyte plate having a pair of electrodes disposed on the upper surface and the lower surface thereof may be vacant, or may have a porous inorganic material packing layer fixedly disposed in the entire space thereof. Alternatively, the diffusion chamber may have a porous inorganic material semi-packing layer fixedly disposed in an upper portion thereof remote from the electrolyte plate, while leaving vacant the remainder of the chamber. The vacant diffusion chamber, the diffusion chamber having the packing layer and the diffusion chamber having the semi-packing layer are shown in FIGS. 2 to 4, respectively.

Figure 1:
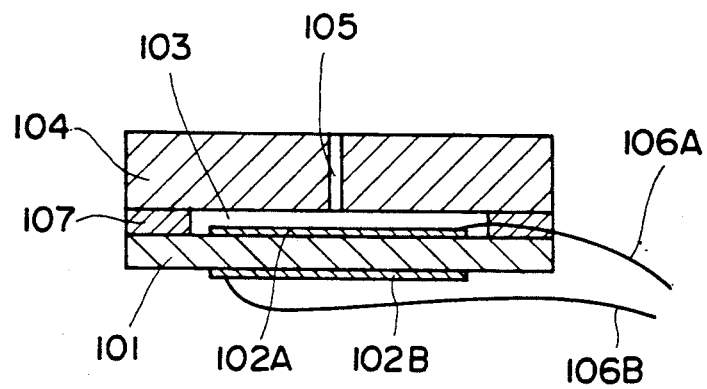
FIG. 1 is a diagrammatic cross-sectional view of a typical form of the conventional oxygen sensor device.
Figure 2:
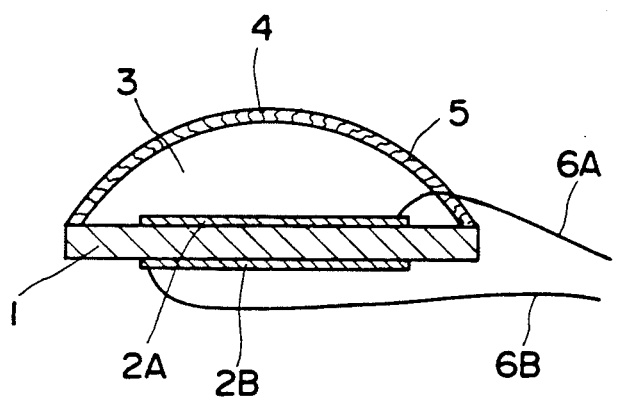
FIG. 2 is a diagrammatic cross-sectional view of one form of the oxygen sensor device of the present invention, in which the diffusion chamber defined by a solid electrolyte plate and a glass dome formed thereon is vacant, the glass dome having cracks as a gas inlet means for diffusing ambient gas into the diffusion chamber.

Referring now to FIG. 2, numeral 1 designates a solid electrolyte plate having oxygen ion conductivity upon energization of the electrolyte, numerals 2A and 2B porous platinum electrodes formed on the surfaces of solid electrolyte plate 1, numeral 4 a glass dome, numeral 5 cracks formed in glass dome 4 as a gas inlet means, and numerals 6A and 6B electric lead means respectively connected to porous electrodes 2A and 2B.

Glass dome 4 and electrode-carrying solid electrolyte plate 1 define vacant diffusion chamber 3.

Figure 3:
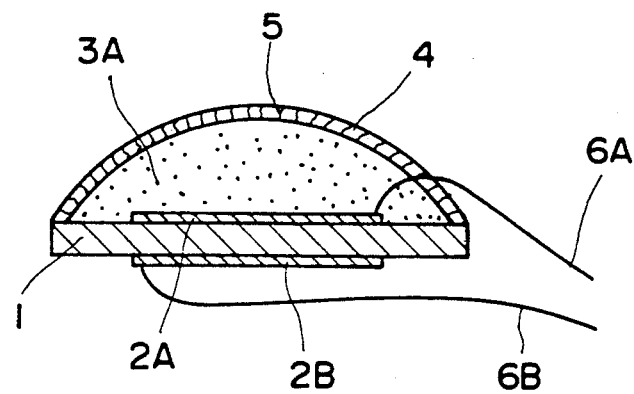
FIG. 3 is a diagrammatic cross-sectional view of another form of the oxygen sensor device of the present invention, which is similar to that of FIG. 1 but in which a porous inorganic material is fixedly disposed in the entire space of the diffusion chamber.
Figure 4:
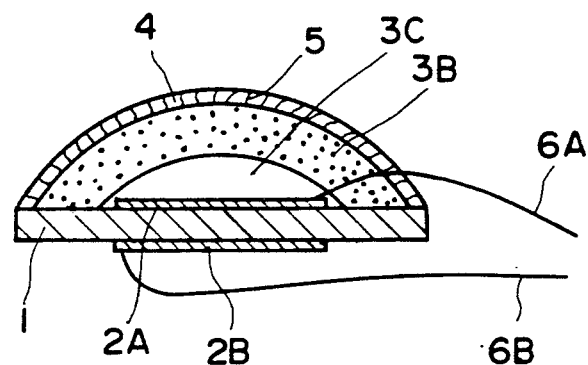
FIG. 4 is a diagrammatic cross-sectional view of still another form of the oxygen sensor device of the present invention, which is similar to that of FIG. 3 but in which a porous inorganic material is fixedly disposed in only an upper portion of the diffusion chamber.

In FIG. 3, porous inorganic material packing layer 3A is fixedly disposed in the entire space of the diffusion chamber defined by glass dome 4 and solid electrolyte plate 1.

In FIG. 4, porous inorganic material semi-packing layer 3B is fixedly disposed in an upper portion of the diffusion chamber defined by glass dome 4 and solid electrolyte plate 1, which upper portion is remote from solid electrolyte plate 1, while leaving vacant the remainder of the diffusion chamber to form vacant portion 3C.

In the oxygen sensor device of the present invention, there are no particular limitations with respect to the thickness of the glass dome, the thickness of the porous inorganic material packing or semi-packing layer and the thickness of the solid electrolyte plate. However, from a practical point of view, the thickness of the glass dome and the thickness of the porous inorganic material packing layer and the thickness of the solid electrolyte plate are generally in the ranges of from 5 to 30 $\mu$m, from 5 to 20 $\mu$m and from 0.1 to 1 mm, respectively. The thickness of the solid electrolyte plate is preferably in the range of from 0.1 to 0.4 mm. In the case of the oxygen sensor device having a porous inorganic material semi-packing layer, the thickness of the vacant portion of the diffusion chamber has no particular limitation, but is generally in the range of from 1 to 5 $\mu$m. When the gas inlet means is provided in the solid electrolyte plate, the diameter of the gas inlet means is generally in the range of from 10 to 100 $\mu$m. When the gas inlet means is provided in the glass dome, the diameter of the gas inlet means is preferably in the range of from 30 to 100 $\mu$m.

With respect to the shape of the glass dome, there is also no limitation. Although the shape of semi-circle in cross-section is shown herein, any other shapes including rectangular shape can be used.

The type of glass for forming the glass dome is not critical. Examples of glass compositions are shown in Table 1.

TABLE 1

| Type of Glass | Composition (% by weight) | | | | | | | | | | | Thermal expansion coefficient $10^{-7}/°C.$ |
|---|---|---|---|---|---|---|---|---|---|---|---|---|
| | Na$_2$O | K$_2$O | BaO | SiO$_2$ | B$_2$O$_3$ | Al$_2$O$_3$ | MgO | CaO | ZnO | PbO | SnO$_2$ | |
| A | | | 12 | 15 | 25 | | 25 | | 20 | | | 100 |
| B | 3 | | 20 | 45 | 2 | | | 10 | | 15 | | 78 |
| C | | | 50 | 30 | 12 | 8 | | | | | | 73 |
| D | | | 35 | 25 | | 20 | | | 15 | | | 99 |
| E | | | 18 | 14 | 25 | | 40 | | | | 1.5 | 125 |

When heated to certain temperatures, some types of glass are crystallized, while other types of glass are not crystallized and remain in an amorphous state. The glass to be used for forming the glass dome of the oxygen sensor device of the present invention can be selected from either of the above-mentioned two different types. Types A, D and E shown in Table 1 are crystallizable. On the other hand, types B and C are non-crystallizable.

In the present invention, if desired, the glass dome may be formed of a plurality of glass layers. As described later, from the viewpoint of power consumption saving, the glass dome preferably has a double layer structure formed of a glass layer of high electrically insulating properties, such as one made of crystallized glass, and a glass layer of high sealing properties, such as one made of non-crystallized glass.

The porous inorganic material packing layer mentioned before is formed of an antifire material which does not melt at the temperature used for forming the glass dome. Representative examples of antifire materials are ceramics (e.g., aluminum oxide, zirconia, calcium oxide, silicon carbide, silicone nitride, spinel, silica, magnesia, mullite) and metals (e.g., iron, nickel, chrome, manganese). The proportion of the volume of the void portion to the entire volume of the diffusion chamber is generally about 20% or higher.

In general, the volume of the diffusion chamber should be as small as possible. The ambient pressure often suffers from sharp increase due to the change of climate, occurrence of bursting of steam, operation of an air conditioner and the like. If the volume of the diffusion chamber is too large and the ambient pressure outside the diffusion chamber is sharply increased, a large amount of ambient gas flows into the diffusion chamber, resulting in a sharp increase in the electric current. The sharp increase in the electric current impairs the functional stability of the sensor device. From this viewpoint, it is preferred that a porous inorganic material packing layer be disposed in the diffusion chamber. On the other hand, the contact area of the electrode on the side of the diffusion chamber with an ambient gas should be as large as possible from the viewpoint of causing the electrode to exert full performance. Accordingly, it is more preferred that a porous inorganic material semi-packing layer be fixedly disposed in an upper portion of the diffusion chamber, while leaving vacant the remainder of the diffusion chamber.

The oxygen sensor device of the present invention may be provided with a heater means for applying heat to the solid electrolyte plate. When the oxygen sensor device of the present invention is not provided with a heater means, an external heater may be employed for facilitating the energization of the solid electrolyte plate.

In the present invention, the glass dome or the solid electrolyte plate has a gas inlet means for diffusing ambient gas into the diffusion chamber. The method for providing a gas inlet means is not critical. A gas inlet means may be provided by forming cracks in the glass dome as shown in FIGS. 2, 3 and 4. In the oxygen sensor device of FIGS. 2, 3 and 4, glass dome 4 has fine cracks 5. Fine cracks 5 can be formed in glass dome 4 by applying heat shock thereto once or twice.

In the oxygen sensor device of FIG. 3, glass dome 4 has fine cracks and porous inorganic material packing layer 3A is fixedly disposed in the entire space of the diffusion chamber defined by glass dome and solid electrolyte plate 1.

Figure 5:
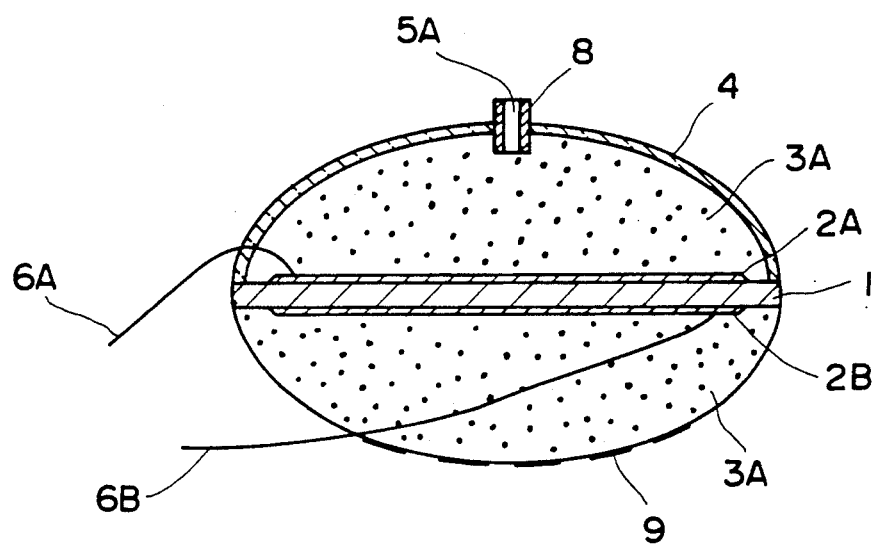
FIG. 5 is a diagrammatic cross-sectional view of a further form of the oxygen sensor device of the present invention, in which the gas inlet means is a capillary planted in the glass dome formed on one side of the solid electrolyte plate and the inorganic material packing layer formed on the opposite side of the solid electrolyte plate has no glass dome thereon but has a heater means disposed directly thereon.

A gas inlet means may alternatively be provided in the glass dome by planting a capillary in the glass dome as shown in FIG. 5. In FIG. 5, the gas inlet means is capillary 8 planted in glass dome 4. In the embodiment of FIG. 5, porous inorganic material packing layer 3A is provided on the opposite side of solid electrolyte plate 1. Heater means 9 is advantageously provided directly on layer 3A. Layer 3A shown in FIG. 5 has no glass dome thereon, however, a glass dome may be formed on layer 3A. In the case of the latter, a gas outlet means is necessarily formed in the glass dome.

As described later, the oxygen sensor device may preferably be produced by a method comprising the steps of (1) providing an oxygen conductive solid electrolyte plate having electrodes and electric lead means disposed thereon, (2) forming a burnable material layer, a porous antifire inorganic material layer or a composite layer of burnable material and antifire inorganic material on the electrolyte plate, (3) coating a powdery glass-containing pasty material on the layer to form a glass-containing layer, and (4) firing the resultant coated plate.

When a capillary is planted in the glass dome, the capillary may simply be planted in the glass dome after step (3) but before step (4). However, when a porous inorganic material packing layer or a porous inorganic material semi-packing layer is employed, the planting of a capillary in the glass dome is likely to cause a pasty material to enter the hollow of the capillary, thereby bringing about the problem of clogging. In order to inhibit the entering of the pasty material into the capillary, the end portion of the capillary may be sealed with an organic material (e.g., epoxy resin, polyimide resin, polyamide resin and polystyrene resin). For sealing the end portion of the capillary, the organic material may be coated on the end portion of the capillary. When the organic material is in a powdery form, the material may be filled into the hollow end portion of the capillary. When firing is performed for formation of the glass dome, the organic material is burnt off to leave open the end portion of capillary 8 while forming a small vacant portion. Such a small vacant portion can also be formed around an aperture formed in the solid electrolyte plate in the similar manner as later described with reference to FIGS. 11(A) and 11(B). The vacant portion formed around the open end portion is effective for promotion of the diffusion of ambient gas into the diffusion chamber. The organic material is required to burn at a temperature higher than the calcination temperature (about 600° C.) for an inorganic material (such as alumina), but lower than the calcination temperature for glass (about 900° to 1000° C.).

Still further, a gas inlet means may be provided in the glass dome by creating an orifice by means of a substance capable of foaming. For example, a gas inlet means is formed in the glass dome by embedding in a glass-containing layer a microsphere of a mixture of a powdery glass-containing pasty material and a substance capable of foaming at the melting temperature of the powdery glass, before the firing, followed by firing to obtain a glass dome having an orifice. Embedding may be performed by using a needle or the like. The mixture may be obtained by mixing the glass material with 1 to 50% by weight of a substance capable of foaming at the melting temperature of the powdery glass, such as sodium nitrite.

Still further, a gas inlet means may be provided in the glass dome by planting in the glass-containing layer a fiber capable of melting or burning at the melting temperature of the powdery glass, followed by firing to obtain a glass dome having an orifice. The fiber may be made of aluminum, magnesium or the like. The fiber may simply be planted in the powdery glass-containing material so that it reaches the burnable material layer or the antifire material layer. The inner end portion of the fiber may optionally be coated with an organic material in the same manner as in the case of the capillary. When firing is performed, the fiber is melted or burnt to form an orifice, and the organic material is burnt off to leave a vacant portion around the inner end portion of the orifice. As described before, the vacant portion is effective for facilitating the diffusion of ambient gas into the diffusion chamber.

Figure 6:
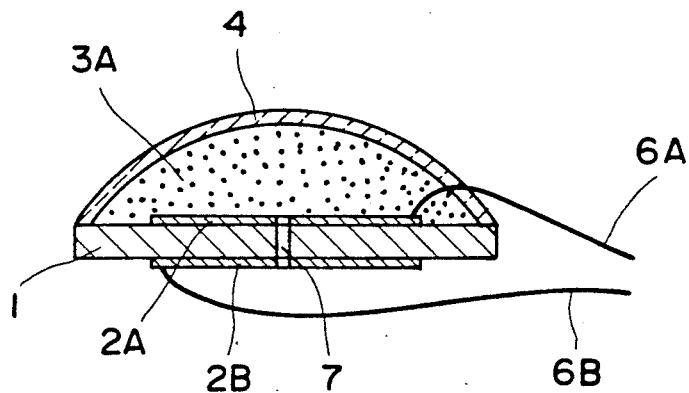
FIG. 6 is a diagrammatic cross-sectional view of still a further form of the oxygen sensor device of the present invention, in which the gas inlet means is an aperture formed in the solid electrolyte plate.

One preferred form of an oxygen sensor device is shown in FIG. 6, which has a solid electrolyte plate provided with a gas inlet means. In FIG. 6, numeral 1 designates an oxygen conductive solid electrolyte plate having a predetermined oxygen ion conductivity upon the energization of the electrolyte, and numerals 2A and 2B designate a first electrode and a second electrode which are porous and made of, for example, platinum and which are respectively disposed on the upper surface and the lower surface of solid electrolyte plate 1. Numeral 7 designates an aperture as a gas inlet means formed in solid electrolyte plate 1, and numeral 3A designates a porous antifire inorganic material packing layer which is formed over first electrode 2A on the upper surface of solid electrolyte plate 1. Numeral 4 designates a glass dome which is formed over the entire surface of porous antifire inorganic material packing layer 3A, and numerals 6A and 6B designate a first electric lead means and a second electric lead means respectively for connecting first electrode 2A and second electrode 2B to power source means.

Figure 11A:
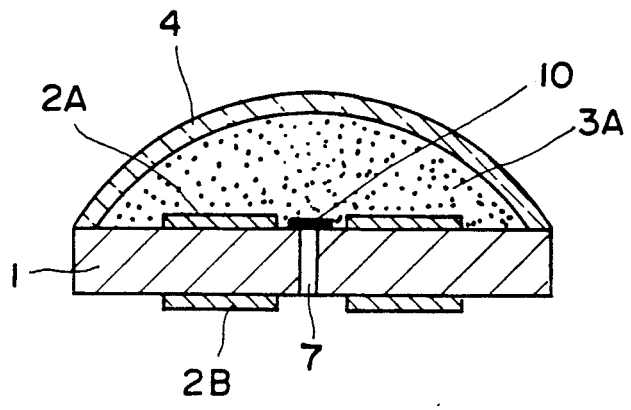
FIG. 11(A) is a diagrammatic view explaining how to prevent the aperture of the solid electrolyte plate from clogging during the formation of a packing layer and a glass dome thereon.
Figure 11:
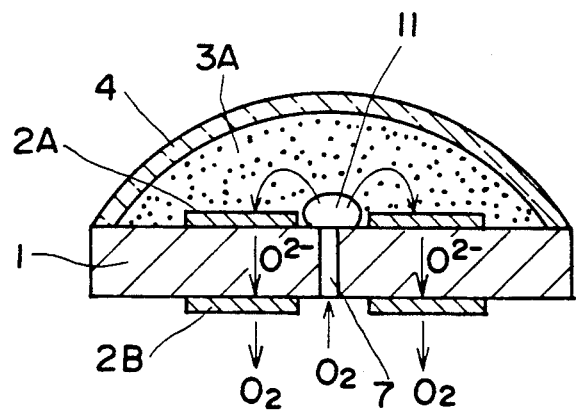

In an oxygen sensor device having a solid electrolyte plate having a gas inlet means, the oxygen sensor device may preferably have a structure such that the gas inlet means is not blocked with a porous antifire inorganic material packing layer. One preferred form of an oxygen sensor device having the above-mentioned structure is shown in FIG. 11(B). For example, the device may be obtained as follows. As is shown in FIG. 11(A), a pasty material containing a powdery metal is coated by screen printing on the upper surface a the lower surface of solid electrolyte plate 1 having aperture 7 and fired to form first electrode 2A and second electrode 2B each made of the metal. Representative examples of powdery metals include powdery platinum, powdery palladium, powdery silver and a mixture thereof. Of these, powdery platinum is preferred. Then, the inner end of aperture 7 is blocked by coating pasty burnable organic material 10 thereon or blocked by placing powdery burnable organic material 10 thereon. Thereafter, a pasty material containing an antifire inorganic material, such as a powdery alumina, is coated over the upper surface of solid electrolyte plate 1 having first electrode 2A thereon, and then fired to form porous antifire inorganic material packing layer 3A. A powdery glass-containing pasty material is coated on the entire surface of the porous antifire inorganic material packing layer 3A and then fired to form glass dome 4, thereby providing a diffusion chamber defined by solid electrolyte plate 1 and glass dome 4 and filled by packing layer 3A. During the firing of the powdery glass-containing pasty material, organic material 10 is burnt off. As a result, as shown in FIG. 11(B), vacant portion 11 is formed around the inner end of aperture 7 where organic material 10 has been present, and the inner end of aperture 7 as a gas inlet means fully opens to a diffusion chamber, thereby enabling pumping of oxygen to be efficiently performed as shown by arrows.

The method for producing an oxygen sensor device of the present invention is not limited to the above but various methods can be employed to obtain various forms of the oxygen sensor device as described hereinbelow.

One form of an oxygen sensor device of the present invention can be produced by method (I) comprising the steps of:

(1) providing an oxygen conductive solid electrolyte plate having a first electrode and a second electrode respectively disposed on the upper surface and the lower surface of the solid electrolyte plate and having a first electric lead means and a second electric lead means respectively for connecting the first and second electrodes to power source means, the solid electrolyte plate having a gas inlet means or having no gas inlet means;

(2) forming a burnable material layer on at least one of the upper and lower surfaces of the solid electrolyte plate;

(3) coating a powdery glass-containing pasty material on the entire surface of the burnable material layer to form a glass-containing layer; and (4) firing the resultant coated plate having the burnable material layer disposed between the glass-containing layer and the solid electrolyte plate, thereby forming a glass dome fluid-tightly connected at its circumferential edge to at least one of the upper and lower surfaces of the solid electrolyte plate, the glass dome defining a vacant diffusion chamber in cooperation with the solid electrolyte plate;

wherein, when the electrolyte plate has no gas inlet means, a gas inlet means is formed in the glass dome simultaneously with or after the firing for formation of the glass dome.

The above-mentioned method is specifically described with reference to FIGS. 7(A) to 7(D).

Figure 7A:
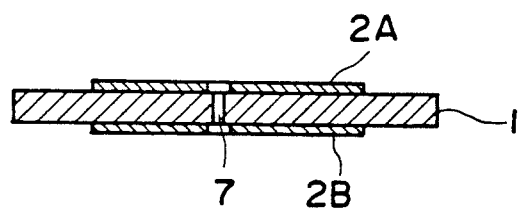
FIG. 7(A) to 7(D) are diagrammatic cross-sectional views to be used for explaining a method for producing an oxygen sensor device of the present invention in which the diffusion chamber is vacant.
Figure 7B:
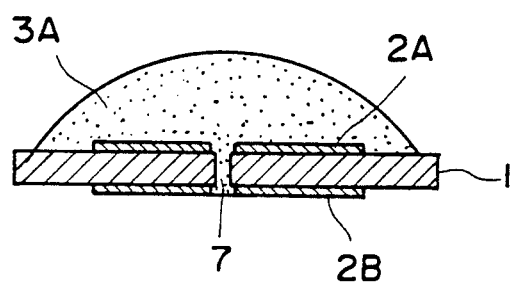

For example, a powdery zirconia containing 8% by mole of a powdery $Y_2O_3$ is incorporated in a rubber tube. In this instance, a yarn made of, for example, a polyester fiber, such as Tetron ® or carbon fiber longitudinally extends under tension through the center line of the rubber tube. The powdery zirconia with the yarn passing therethrough is compressed under a pressure of, for example, about 1000 kg/cm². The compressed zirconia is taken out of the rubber tube and fired at 1600° C. for 3 hours to obtain a rod-shaped fired zirconia product having an aperture passing therethrough. The rod-shaped fired zirconia product is sliced in a perpendicular direction to the aperture to obtain a slice having an aperture running through the slice from one surface thereof to the other surface thereof. The slice with the aperture constitutes solid electrolyte plate 1 with gas inlet means 7. On each surface of the slice as solid electrolyte plate 1 is coated by screen printing a pasty material containing a powdery metal prepared in substantially the same manner as in the preparation of a powdery glass-containing pasty material except that a powdery metal having a diameter of from 0.1 μm to several hundreds of microns (μm), preferably from 0.1 to 10 μm, is used instead of a powdery glass. Representative examples of powdery metals include powdery platinum, powdery palladium, powdery silver and a mixture thereof. Of these, powdery platinum is preferred. The resultant plate is fired at about 1000° C. for about 30 minutes to obtain solid electrolyte plate 1 having gas inlet means 7 and having first electrode 2A on its upper surface and second electrode 2B on its lower surface. The thus obtained solid electrolyte plate 1 is shown FIG. 7(A). Then, as shown in FIG. 7(B), a pasty material containing a burnable material, such as aluminum powder, magnesium powder, a burnable synthetic resin, carbon or graphite, is coated by screen printing on the upper surface of solid electrolyte plate 1 having first electrode 2A thereon to form burnable material layer 3A. Representative examples of synthetic resins include a polyimide resin, a polyamide resin, a polyester resin and an epoxy resin. During the course of the screen printing, gas inlet means 7 is generally clogged with the pasty material containing a burnable material as shown FIG. 7(B). However, it sometimes occurs that gas inlet means 7 is not clogged with the pasty material containing a burnable material, because the diameter of gas inlet means 7 is as small as from about 20 to about 30 $\mu$m. Whichever occurs, the consequence is the same, because the pasty material is burnt off or vaporized during the firing described below.

Figure 7C:
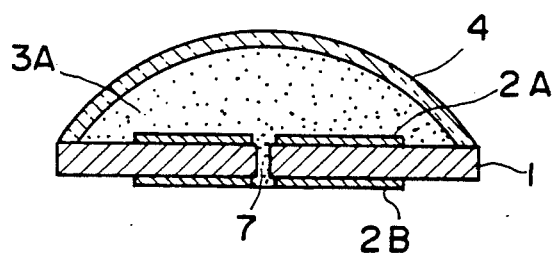
Figure 7D:
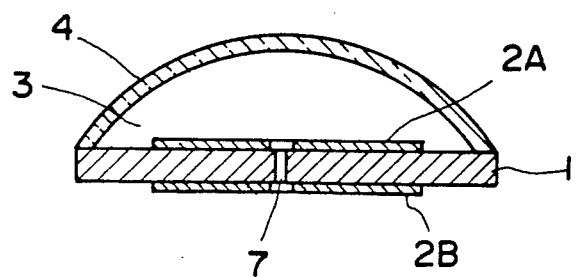

Thereafter, as shown in FIG. 7(C), a powdery glass-containing pasty material is coated on burnable material layer 3A by screen printing to form glass-containing layer 4 completely covering burnable material layer 3A. The pasty material may be prepared for example by mixing a powdery glass having a diameter of 0.1 to 20 $\mu$m with a mixture of butylcarbitol acetate and nitrocellulose in proportions such that the weight ratio of the powdery glass to the solvent is 1:1 to form glass-containing layer 4 completely covering antifire inorganic material layer 3A. Representative examples of powdery glasses include glasses shown in Table 1 shown above. Such glasses generally have a thermal expansion coefficient of from $70 \times 10^{-7}$ to $130 \times 10^{-7}/°$ C. Specific examples of glasses having a thermal expansion coefficient of from $70 \times 10^{-7}$ to $130 \times 10^{-7}/°$ C. include crystalline glass AP5710 (produced and sold by Asahi Glass Co., Ltd., Japan). It is preferred that glass dome 4 have a thermal expansion coefficient close to that of solid electrolyte plate 1. However, it is not always necessary that the thermal expansion coefficient of glass dome 4 be equal to that of solid electrolyte plate 1. For example, the thermal expansion coefficient of glass dome 4 is generally in the range of $70 \times 10^{-7}$ to $130 \times 10^{-7}/°$ C. and the thermal expansion coefficient of solid electrolyte plate 1 is generally in the range of $95 \times 10^{-7}$ to $100 \times 10^{-7}/°$ C. The resultant composite may be subjected to provisional firing for drying, followed by final firing. Alternatively, the resultant composite may directly be subjected to final firing without provisional firing. The final firing is performed, for example, in a furnace at 600° to 1000° C. for about 30 minutes so that glass-containing layer 4 is converted into a glass layer [shown in FIG. 7(D) as glass dome 4]fluid-tightly connected at its circumferential base edge to the upper surface of solid electrolyte plate 1. As a result, as shown FIG. 7(D), glass dome 4 defining diffusion chamber 3 in cooperation with solid electrolyte plate 1 having aperture 7, is formed.

An oxygen sensor device comprising a porous inorganic material packing layer which is fixedly disposed in the entire space of a diffusion chamber defined by an oxygen conductive solid electrolyte plate provided with a pair of electrodes and a glass dome can efficiently be produced by, for example, the following method (II).

Method (II) comprises the steps of:

(1) providing an oxygen conductive solid electrolyte plate having a first electrode and a second electrode respectively disposed on the upper surface and the lower surface of the solid electrolyte plate and having a first electric lead means and a second electric lead means respectively for connecting the first and second electrodes to power source means, the solid electrolyte plate having a gas inlet means or having no gas inlet means;

(2) forming a porous antifire inorganic material layer on at least one of the upper and lower surfaces of the solid electrolyte plate;

(3) coating a powdery glass-containing pasty material on the entire surface of the antifire material layer to form a glass-containing layer; and (4) firing the resultant coated plate having the porous antifire inorganic material layer disposed between the glass-containing layer and the solid electrolyte plate, thereby forming a glass dome fluid-tightly connected at its circumferential base edge to the upper surface of the solid electrolyte plate, the glass dome defining in cooperation with the solid electrolyte plate a diffusion chamber having a porous antifire inorganic material packing layer fixedly disposed in the entire space of the diffusion chamber;

wherein, when the electrolyte plate has no gas inlet means, a gas inlet means is provided in the glass dome simultaneously with or after the firing for formation of the glass dome.

The above-mentioned method is specifically described with reference to FIGS. 7(A) to 7(C).

Substantially the same procedure as in method (I) is repeated to obtain solid electrolyte plate 1 having gas inlet means 7 and having first electrode 2A on its upper surface and second electrode 2B on its lower surface. The thus obtained solid electrolyte plate 1 is shown in FIG. 7(A). Then, a powder of an antifire inorganic material, for example, a ceramic, such as alumina or zirconia, or a metal, such as titanium or iron, is mixed with a solvent, such as water, an alcohol, $\alpha$-terpineol or the like to obtain a pasty material containing an antifire inorganic material. As shown in FIG. 7(B), the pasty material containing an antifire inorganic material is coated by screen printing on the upper surface of solid electrolyte plate 1 having first electrode 2A thereon to form antifire inorganic material layer 3A. The resultant composite is fired at about 1000° C. or dried. Then, coating of a powdery glass-containing pasty material and firing are performed in substantially the same manner as in method (I). As a result, the desired oxygen sensor device having a porous antifire inorganic material packing layer disposed in the entire inner space of the glass dome is obtained.

An oxygen sensor device comprising a porous inorganic material semi-packing layer which is fixedly disposed in an upper portion of a diffusion chamber which portion is remote from a solid electrolyte plate, while leaving vacant the remainder of a diffusion chamber defined by the solid electrolyte plate, which is provided with a pair of electrodes, and a glass dome, can be efficiently produced by, for example, the following method (III).

Method (III) comprises the steps of:

(1) providing an oxygen conductive solid electrolyte plate having a first electrode and a second electrode respectively disposed on the upper surface and the lower surface of the solid electrolyte plate and having a first electric lead means and a second electric lead means respectively for connecting the first and second electrodes to power source means the solid electrolyte plate having a gas inlet means or having no gas inlet means;

(2) forming a burnable material layer on at least one of the upper and lower surfaces of the solid electrolyte plate;

(3) forming a porous antifire inorganic material layer on the burnable material layer;

(4) coating a powdery glass-containing pasty material on the entire surface of the antifire material layer to form a glass-containing layer; and (5) firing the resultant coated plate having the burnable material layer and the porous antifire inorganic material layer disposed thereon between the glass-containing layer and the solid electrolyte plate, thereby forming a glass dome fluid-tightly connected at its circumferential base edge to the upper surface of the solid electrolyte plate, the glass dome defining in cooperation with the solid electrolyte plate a diffusion chamber having a porous antifire inorganic material semi-packing layer fixedly disposed in an upper portion of the diffusion chamber which upper portion is remote from the solid electrolyte plate, while leaving vacant the remainder of the diffusion chamber;

wherein, when the electrolyte plate has no gas inlet means, a gas inlet means is formed in the glass dome simultaneously with or after the firing for formation of the glass dome.

The above-mentioned method is specifically described with reference to FIG. 4.

Substantially the same procedure as in method (I) is repeated to obtain solid electrolyte plate 1 having first electrode 2A on its upper surface and second electrode 2B on its lower surface. Then, a burnable material layer is formed in a predetermined thickness in substantially the same manner as in method (I). Thereafter, on the burnable material layer is coated by screen printing a pasty material containing an antifire inorganic material as used in method (II) in a predetermined thickness to form an antifire material layer 3B completely covering the burnable material layer. The resultant composite is fired at about 1000° C. or dried. On the resultant composite is coated by screen printing a powdery glass-containing pasty material as used in method (I) to form a glass-containing layer 4 completely covering the antifire inorganic material layer 3B. The resultant composite is fired at 600° to 1000° C. for about 30 minutes to form glass dome 4 fluid-tightly connected at its circumferential base edge to the upper surface of solid electrolyte plate 1, thereby forming a diffusion chamber defined by solid electrolyte plate 1 and glass dome 4.

In the firing, the burnable material layer is burnt while supporting antifire inorganic material layer 3B until antifire inorganic material layer 3B becomes firm and porous. The burnable material layer is finally burnt off. As a result, there is provided porous inorganic material semi-packing layer 3B which is fixedly disposed in an upper portion of the diffusion chamber which portion is remote from solid electrolyte plate 1, while leaving vacant the remainder of the diffusion chamber. When the burnable material is relatively slowly burnable material, antifire inorganic material layer is firmly supported by the burnable material layer. Therefore, it is preferred to use a relatively slowly burnable material. Representative examples of relatively slowly burnable materials include carbon and graphite.

The above description is made with respect to the oxygen sensor device having a gas inlet means in an oxygen conductive solid electrolyte plate. Of course, an oxygen sensor device having a gas inlet means in a glass dome can be produced by simply changing the manner of providing a gas inlet means. The method for providing the glass dome with a gas inlet means is as described hereinbefore.

As mentioned before, it is preferred that an oxygen sensor device be provided with a heater means having a third electric lead means and a fourth electric lead means respectively for connecting the heater means to power source means. A heater means may be provided inside or outside the diffusion chamber. For example, a heater means may be disposed on the inner wall surface or on the outer wall surface of a glass dome. When a heater means is provided inside the diffusion chamber, it is preferred that an oxygen sensor device further comprise an electrically insulating porous glass layer provided between the heater means and the first electrode disposed on the upper surface of the solid electrolyte plate. When a heater means is disposed on the inner wall surface or the outer wall surface of the glass dome, the glass dome is required to have sufficient electrically insulating properties for preventing electrical leak from the heater means. The prevention of electrical leak from the heater means contributes to not only high performance of the oxygen sensor device but also energy saving. On the other hand, it is preferred from the viewpoint of attaining high accuracy of an oxygen sensor device that the glass dome have good sealing properties. Therefore, when a heater is disposed on the inner wall surface or the outer wall surface of a glass dome, it is desired for the glass dome to have both sufficient electrically insulating properties and good sealing properties. If a glass dome comprising a single glass layer does not have both sufficient electrically insulating properties and good sealing properties, it is preferred to use a glass dome having a double layer structure, i.e., a glass dome comprising a glass layer of high electrically insulating properties and a glass layer of high sealing properties. When a glass dome having a double layer structure is used, a heater is disposed on the surface of the glass layer of high electrically insulating properties. That is, the glass layer of high electrically insulating properties is in contact on one side thereof with the glass layer of high sealing properties and on the other side thereof with the heater means.

Figure 8:
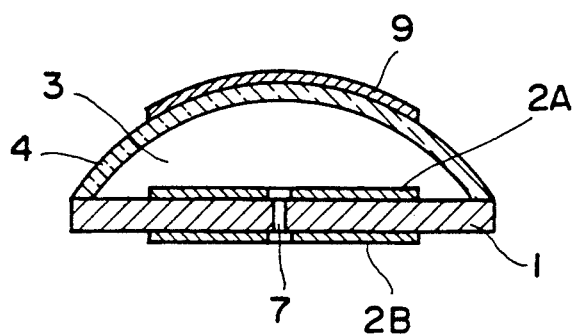
FIG. 8 is a diagrammatic cross-sectional view of still a further form of the oxygen sensor device of the present invention, in which a heater means is disposed on the outer wall surface of the glass dome.

The method for disposing a heater means is not critical. For example, a heater means can be disposed on the outer wall surface of a glass dome according to the following method which is described with reference to FIG. 8. On glass dome 4 of an oxygen sensor device is coated by screen printing, dipping or spraying a pasty material containing a powdery metal, which is prepared in substantially the same manner as in the preparation of the powdery glass-containing pasty material, except that a powdery metal is used instead of a powdery glass. Representative examples of powdery metals include powdery platinum, powdery palladium, powdery silver and a mixture thereof. Of these, powdery platinum is preferred. Then, the coated glass dome is fired to obtain an oxygen sensor device provided with heater means 9 on its outer wall surface of glass dome 4.

Figure 9:
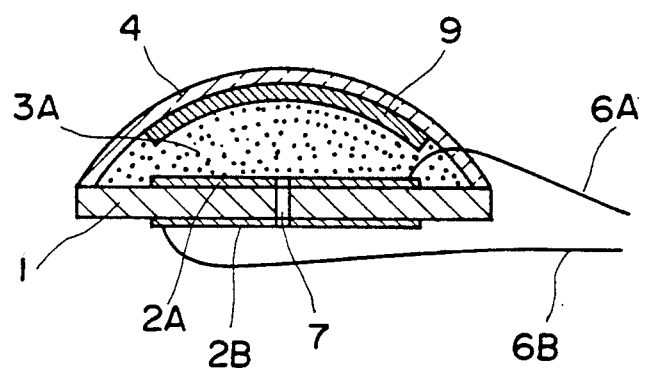
FIG. 9 is a diagrammatic cross-sectional view of still a further form of the oxygen sensor device of the present invention, in which a heater means is disposed on the inner wall surface of the glass dome.

Further, a heater means can be disposed on the inner wall surface of a glass dome according to the following method which is described with reference to FIG. 9. On the upper surface of solid electrolyte plate 1 having gas inlet means 7 and having first electrode 2A on its upper surface and second electrode 2B on its lower surface is coated by screen printing, dipping or spraying a pasty material containing an antifire inorganic material, e.g., alumina or zirconia, to form antifire inorganic material layer 3A. Antifire inorganic material layer 3A is dried, and the above-mentioned pasty material containing a powdery metal for forming heater means is coated thereon by screen printing, dipping or spraying, and fired. Then, a powdery glass-containing pasty material is coated, and fired. As a result, an oxygen sensor device having heater means 9 disposed on the inner wall surface of glass dome 4 as shown in FIG. 9 is obtained.

Subsequently, a powdery platinum-containing pasty material is coated on the surface of the above-mentioned porous antifire inorganic material layer 3A formed on the upper surface of solid electrolyte plate 1, followed by drying to form a platinum layer. The coating of a powdery platinum-containing pasty material may be conducted by printing or spraying the pasty material. Alternatively, the coating of the pasty material may be conducted by dipping the surface of the porous antifire inorganic material layer 3A in the pasty material. On the entire surface of the resultant platinum layer, a powdery crystallizable glass-containing pasty material is coated by printing, dipping, spraying or the like in the manner as mentioned above. The resultant ion conductive plate comprising the solid electrolyte plate and, coated thereon, the inorganic material layer, the platinum layer and the glass-containing layer is fired so that the platinum layer is sintered to form heater means 9 bonded to the surface of inorganic material layer 3A, and the crystallizable glass of the glass-containing layer is simultaneously crystallized to form a glass layer in the form of glass dome 4. Thus, an oxygen sensor device which has a heater means disposed on the inner wall surface of the glass dome is obtained. When a heater means is provided on the inside of a glass dome, it is preferred that an electrically insulating porous glass layer be provided between the heater means and the first electrode disposed on the upper surface of the solid electrolyte plate.

Figure 10:
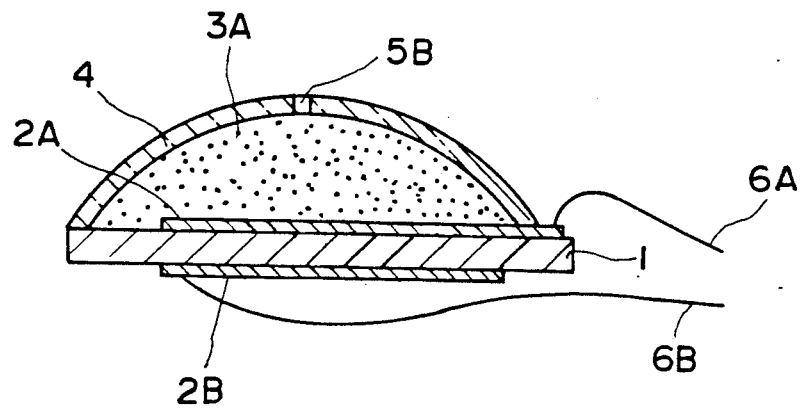
FIG. 10 is a diagrammatic cross-sectional view of still a further form of the oxygen sensor device of the present invention, in which a portion of the first electrode protrudes outside the glass dome.

According to the present invention, the first electrode, namely the electrode provided on the upper surface of a solid electrolyte plate on the side of a diffusion chamber defined by the glass dome and the solid electrolyte plate, may be disposed completely within the glass dome. In this case, the electric lead means needs to be drawn out of the diffusion chamber. This drawing can be done simultaneously with the formation of a glass dome Alternatively, as shown in FIG. 10, the first electrode may be provided such that a portion of the first electrode protrudes outside the glass dome.

In order to prevent breakage of an electric lead means connecting an electrode or a heater means to power source means by shock, impact, etc., and in order to fix the oxygen sensor device easily to a support plate or the like as will be explained later, an oxygen sensor device may further comprise an electrically insulating leg member having attached at its one end portion to the outer surface of the glass dome or the outer surface of the solid electrolyte plate through an adhesive layer, while leaving unattached the remaining elongate portion A couple of the first and second electric lead means and a couple of the third and fourth electric lead means each extend on and along the unattached elongate portion of the leg member, and the gas inlet means and the leg member satisfy a positional relationship such that a passage is provided for diffusing ambient gas into the diffusion chamber through the gas inlet means. The adhesive layer is non-porous or porous in accordance with the position of the gas inlet means relative to the leg member so that a passage is provided for passing the oxygen pumped out of the diffusion chamber through the solid electrolyte plate to ambient atmosphere. Such a device can advantageously be connected to the connector means of power source means by simple engagement of the end portion of the leg member with the connector means, to provide connections between the electric lead means and the power source means, which are unlikely to easily be broken The solid electrolyte plate and the heater means may be provided on the same surface of the leg member. Alternatively, the solid electrolyte plate and the heater means may be separately provided on both surfaces of the leg member, respectively Referring to FIGS. 12(A), (B) and (C), one form of the oxygen sensor device of the present invention comprising a leg member attached to the outer surface of the glass dome through an adhesive layer and in which the gas inlet means is provided in the solid electrolyte plate is explained below. A thin solid electrolyte plate 1 may be made of, for example, a stabilized zirconia (e.g., $ZrO_2\text{-}8Y_2O_3$), having an ionic conductivity. First and second electrodes 2A and 2B are disposed respectively on the lower surface and the upper surface of the solid electrolyte plate. Porous inorganic material packing layer 3A and glass dome 4 are provided on the lower side of the solid electrolyte plate. Solid electrolyte plate 1 has gas inlet means 7 at its center portion and electrodes 2A and 2B have through-hole 2C at their center portion so that ambient gas can be introduced into the diffusion chamber defined by solid electrolyte plate 1 and glass dome 4 through gas inlet means 7 and through-hole 2C. The diameter of the through-hole of the electrode may generally be larger than that of gas inlet means 7. Gas inlet means 7 controls the introduction of ambient gas into the diffusion chamber defined by glass dome 4 and solid electrolyte plate 1 so that the diffusion rate of a gas into the diffusion chamber is controlled. Solid electrolyte plate 1, electrodes 2A and 2B, porous inorganic material layer 3A and glass dome 4 constitute composite 14. An end portion of the electrode disposed in the diffusion chamber protrudes out of the glass dome. To the electrodes, a predetermined electric voltage (for example, about 2 V) is applied. On the outer surface of solid electrolyte plate 1 (lower side in FIG. 12(A)), heater means 9 is provided to heat solid electrolyte plate 1.

Porous inorganic material packing layer 3A is composed of porous sintered material, such as an alumina powder, which is provided so as to cover first electrode 2A completely, and glass dome 4 is provided so as to cover porous sintered material 3A completely. At the center portion of solid electrolyte plate 4, gas inlet means 7 is provided. In this embodiment, the gas inlet means is an aperture running through solid electrolyte plate 1 from one surface thereof to the other surface thereof Ambient gas containing oxygen can be introduced into the diffusion chamber defined by glass dome 4 and solid electrolyte plate 1 through aperture 7. The gas inlet means is not limited to that shown in FIG. 12. The gas inlet means may alternatively be provided in glass dome 4 as mentioned hereinbefore.

In a portion of solid electrolyte plate 1 which is positioned between two electrodes 2A and 2B, a current of oxygen ions is flowed when ambient gas containing oxygen is introduced into the diffusion chamber through gas inlet means 7 and the oxygen is contacted with electrode 2A, so that the oxygen pumped out of the diffusion chamber through the solid electrolyte plate to ambient atmosphere as shown by arrows. By the ionic current, an electric current is caused to flow between the first and second electrodes 2A and 2B. Based on the electric current produced by the ionic current, the partial pressure of oxygen in the ambient gas is determined.

Leg member 15 may generally be made of a material having a thermal expansion coefficient almost equal to that of solid electrolyte plate 1. Examples of materials for leg member 15 include $ZrO_2$-$3Y_2O_3$, $Al_2O_3$ (alumina), forsterite and the like. When the substrate material of leg member 15 is electrically conductive, an alumina powder or a crystallizable glass is coated on the overall surface of leg member 15 by sinter-coating to form an electrically insulating layer. Composite 14 is attached at one end portion on upper surface 15A of leg member 15 by means of adhesive layer 16, and heater means 9 is attached at the same end portion of leg member 15 at its lower surface by printing or plating. When the leg member made of alumina or forsterite is used, it is not necessary to form an electrically insulating layer on the surface thereof.

Adhesive layer 16 is formed by sinter-coating an adhesive at 500° to 1000° C.

Figure 12A:
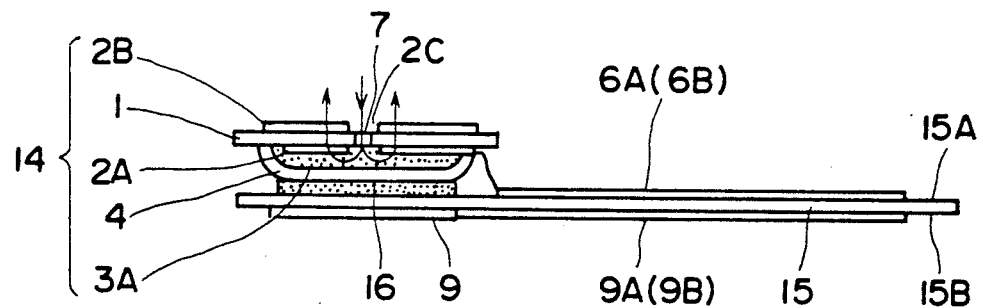
FIGS. 12(A), 12(B) and 12(C) are, respectively, a diagrammatic cross-sectional side view, a diagrammatic plan view, and a diagrammatic bottom view of still a further form of the oxygen sensor device of the present invention, which further comprises a leg member attached at its one end portion to the outer surface of the glass dome through an adhesive layer and in which the gas inlet means is provided in the solid electrolyte plate.
Figure 13:
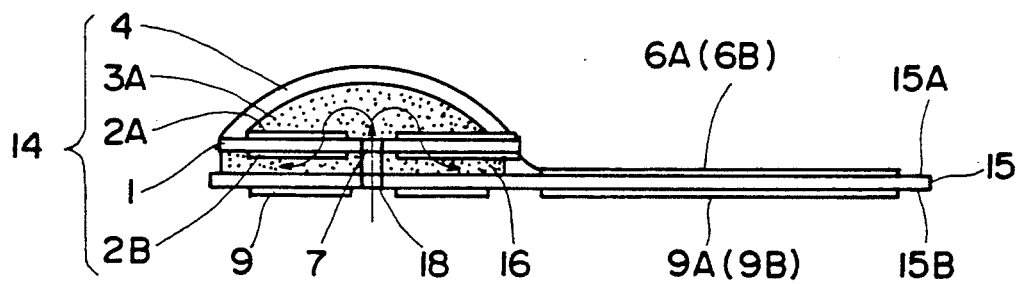
FIG. 13 is a diagrammatic cross-sectional side view similar to 12(A) but in which the leg member and adhesive layer have through-holes in registry with the aperture of the solid electrolyte plate.

In the present invention, the adhesive layer may be non-porous or porous in accordance with the position of the gas inlet means relative to the leg member so that a passage is provided for passing the oxygen pumped out of the diffusion chamber through the solid electrolyte plate to ambient atmosphere. For example, when gas inlet means 7 is provided in solid electrolyte plate 1 and leg member 15 is disposed on the outer surface of solid electrolyte plate 1 as shown in FIG. 13, it is necessary that adhesive layer 16 be porous. On the other hand, when gas inlet means is provided in solid electrolyte plate 1 and leg member 15 is disposed on the outer surface of glass dome 4 as shown in FIG. 12(A), adhesive layer 16 may be either non-porous or porous. However, a porous adhesive layer is advantageous in that the distortion due to the difference in thermal expansion coefficient between glass dome 4 and leg member 15 or between solid electrolyte plate 1 and leg member 15 can be diminished. Therefore, a porous adhesive layer may generally be used. Examples of adhesives include a ceramic type adhesive containing an alkali ion, a mixture of alumina powder with glass, metal paste and the like. When solid electrolyte plate 1 has almost the same thermal expansion coefficient as that of leg member 15, a glass having a thermal expansion coefficient which is almost equal to that of solid electrolyte plate 1 or leg member 15 may also be used as an adhesive. The adhesive may be spotwise coated on the outer surface of glass dome 4 or solid electrolyte plate 1. Alternatively, the adhesive may be coated broadly on the outer surface of glass dome 4 or solid electrolyte plate 1.

Figure 12B:
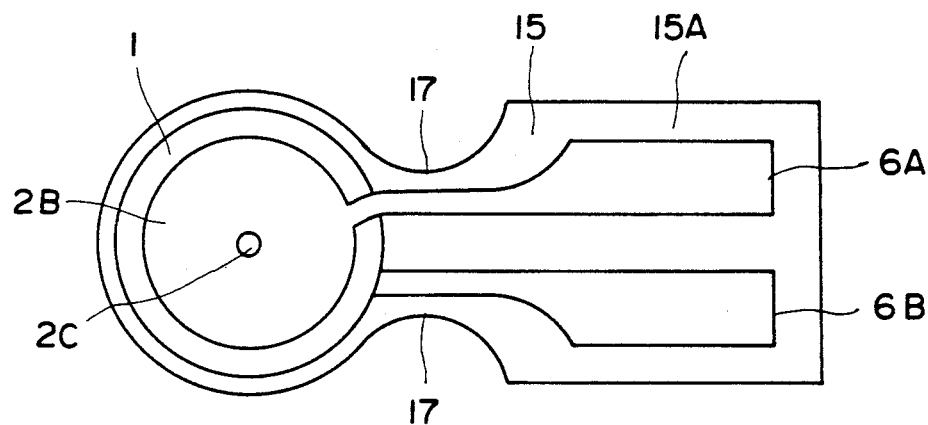
Figure 12C:
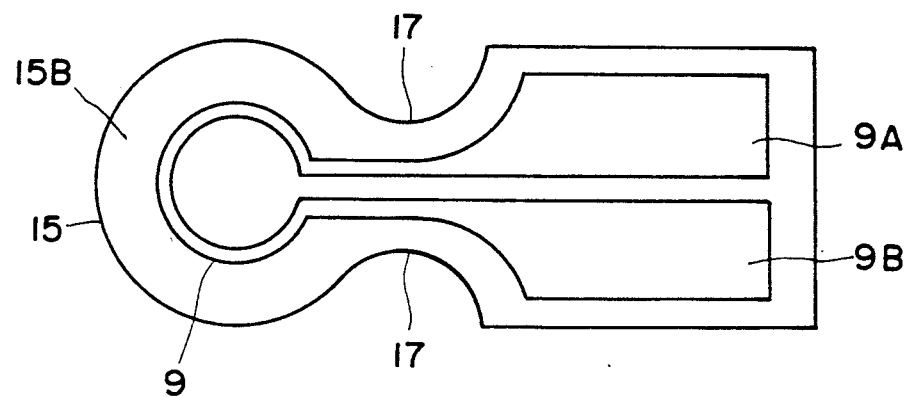

In the embodiment of FIGS. 12(A) to 12(C), electric lead means 6A and 6B respectively connected to electrodes 2A and 2B are disposed on upper surface 15A of leg member 15, whereas electric lead means 9A and 9B respectively connected to heater means 9 are disposed on lower surface 15B of leg member 15.

These electric lead means 6A, 6B, 9A and 9B may be formed by bonding wires or by printing an electrically conductive pasty material, followed by sinter-coating. In FIGS. 12(A), (B) and (C), each of a couple of electric lead means 6A and 6B connected to electrodes 2A and 2B, and a couple of electric lead means 9A and 9B connected to heater means 9 is formed of a pair of parallely running conductive platinum coatings formed on leg member 15 as shown in FIGS. 12(B) and (C).

If desired, neck portion 17 may be as depicted in FIGS. 12(B) and 12(C), so that escape of heat generated by heater means 9 is suppressed.

For not only preventing escape of heat generated by heater means 9, but also attaining uniform heat distribution on solid electrolyte plate 1, neck portion 17 of each of electric lead means 9A and 9B connected to heater means 9 is effective, because heat is generated in neck portion 17 of electric lead means 9A and 9B.

In the oxygen sensor device as shown in FIG. 12, the outer surface of glass dome 4 is attached to leg member 15 through adhesive layer 16.

Alternatively, however, various configurations can be employed. For example, as shown in FIG. 13, the outer surface of solid electrolyte plate 1 which is opposite to the side on which glass dome 4 is formed, may alternatively be attached to leg member 15 through porous adhesive layer 16.

In the embodiment of FIG. 13, each of leg member 15 and adhesive layer has through-hole 18 communicating with aperture 7 of solid electrolyte plate 1.

Figure 14:
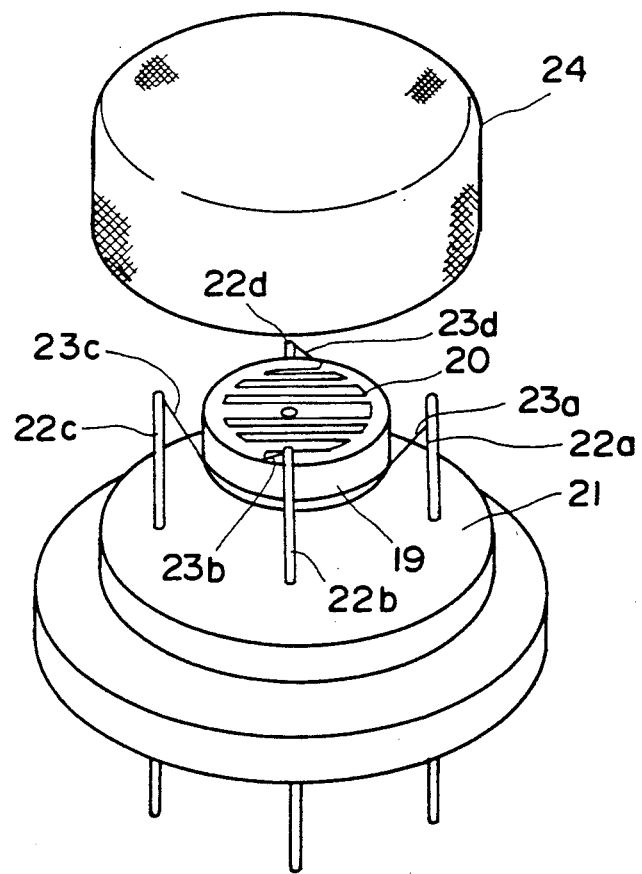
FIG. 14 is a diagrammatic perspective view explaining the conventional manner for disposing an oxygen sensor device in a casing.

As shown in FIG. 14, the oxygen sensor device of the present invention may be secured on a conventional support plate 21 and covered with netted cap 24. In FIG. 14, four pins 22a, 22b, 22c and 22d are fluid-tightly, fixedly planted on discoid support plate 21. Pins 22a and 22c are connected to electric lead means 23a and 23c, respectively, which in turn are connected to two electrodes 2A and 2B (not shown), respectively. Pins 22b and 22d are connected to electric lead means 23b and 23d, respectively, which in turn are connected to both ends of heater means 20, respectively. Electric lead means 23a, 23b, 23c, and 23d may generally be a gold string or a platinum string having a diameter of about 0.1 mm. Oxygen sensor device 19 is suspended in midair by means of four electric lead means 23a, 23b, 23c and 23d, and is wrapped by, for example, a bulk of a fibrous soft substance (not shown) and covered with netted cap 24. However, the structure shown in FIG. 14 has a disadvantage in that when the device receives a shock or impact, the electric lead means occasionally cannot resist the weight of the device so that the electric lead means are broken. Further, the fluid-tight connection between each of pins 22a, 22b, 22c and 22d and support plate is likely to be damaged by shock or impact. When the support plate is set on the wall of a chamber such that the oxygen sensor device on the support plate faces the space of the chamber and the opposite side of the support plate faces the outside of the chamber, and a gap is formed between each pin and support plate by the damage of the fluid-tight connection therebetween which is caused by shock or impact, a gas is introduced from the outside of the chamber into the chamber through the gap so that the partial pressure of the oxygen in the original ambient gas in the chamber no longer can be measured accurately. Further, if the ambient gas in the chamber is harmful, there is a danger that such a harmful gas leaks out of the chamber through the gap. Further, it takes much time for connecting electric lead means to pins, leading to a increase in production cost.

Figure 15A:
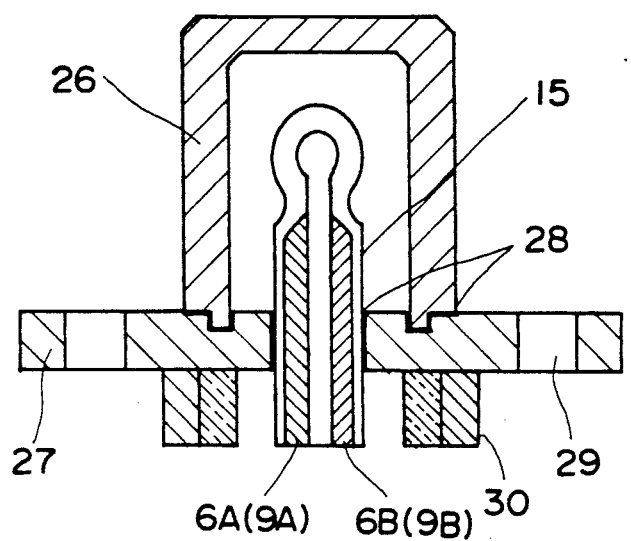
FIG. 15(A) is a diagrammatic cross-sectional side view of still a further form of the oxygen sensor device of the present invention, which is constructed into a unit in which the leg member is fixedly inserted in a slit of a support plate and fixed thereto, with a free end portion of the leg member being protruded through the slit for being easily connected to the connector means of power source means.

The above-mentioned problems can be overcome by fluid-tightly, fixedly inserting the unattached elongate portion of the leg member in the slit of a support plate together with both the couples of electric lead means so that a predetermined length of the elongate portion is protruded, together with the corresponding lengths of both the couples of electric lead means, through the support plate, and covering, with a gas permeable cap, an assembly of the glass dome, the solid electrolyte plate having the first and second electrodes and a portion of the leg member with the corresponding lengths of both the couples of electric lead means, which assembly is positioned above the support plate on the side of the gas permeable cap, leaving a space between the gas permeable cap and the assembly, as shown in FIG. 15(A). The gas permeable cap is fluid-tightly fixed at its circumferential base edge to the upper surface of the support plate. The protruded elongate portion of the leg member is adapted to be connected to a connector means of the power source means.

Referring to FIGS. 15(A) and (B), support plate 27 is made of a ceramic and has, at its center portion, slit 27A for inserting the substrate plate together with both the couples of electric lead means thereinto. Support plate 27 also has, on its surface, groove 26A for receiving and fixing a gas permeable cap thereto. Support plate 27 further has through-holes 29 which are used for fixing the support plate 27 on a wall etc. by means of a bolt and nut or the like. Further, support plate 27 also has connection aid member 30 useful in engaging the free end of the leg member with the connector means of power source means. The assembly is inserted in slit 27A of support plate 27 so that a predetermined length of the elongate portion is protruded together with both the couples of electric lead means through the support plate and fluid-tightly fixed by means of sealing means 28. The gas permeable cap 26 is fluid-tightly fixed at its circumferential base edge to groove 26A by means of sealing means 28. The type of the sealing means is not specifically limited. Generally, a glass may be used. Gas permeable cap 26 may generally be made of a ceramic and porous. The protruded elongate portion of the leg member is adapted to be connected to a connector means of a power source means. The connection may be conducted simply by inserting it in a female connector with the aid of connection aid member 30. Alternatively, the protruded end portion may be connected to a connector by soldering or ultrasonic welding. Ambient gas containing oxygen is introduced into the inner space of gas permeable cap 26 through pores of gas permeable cap 26, and the partial pressure of the oxygen in the ambient gas is measured by the assembly. The above-mentioned structure shown in FIG. 15(A) is excellent in resistance to shock and impact. Therefore, the oxygen sensor device of this type can advantageously be used for measuring the partial pressure of the oxygen in ambient gas with high accuracy over a prolonged period of time.

The oxygen sensor device of the present invention is compact and excellent in reliability, and can be used with low electric demand. The oxygen sensor device of the present invention can easily be produced by a printing technique on a commercial scale without using an adhesive for providing a diffusion chamber on the surface of a solid electrolyte plate, differing from the production of a conventional oxygen sensor device. When an adhesive is used for attaching a housing on the surface of an electrolyte plate to form a diffusion chamber as in the conventional oxygen sensor device, it is disadvantageous in that the housing is likely to slide on the surface of an electrolyte plate before an adhesive disposed between the housing and the electrolyte plate is solidified, so that the circumferential base edge cannot be accurately bonded to the predetermined portion on the surface of the electrolyte plate. Therefore, defective products are produced at high ratio. Further, it is disadvantageous in that the cracking of the adhesive layer provided between a housing and an electrolyte plate is likely to occur when it is used under severe conditions for a long time, leading to a leakage of a gas from the diffusion chamber. Therefore, an accurate oxygen concentration of ambient gas cannot be conducted. However, as mentioned above, the oxygen sensor device of the present without using an adhesive. Therefore, the oxygen sensor device of the present invention is free from the above-mentioned disadvantages. Further, the oxygen sensor device of the present invention has an advantage in that the glass dome of the device of the present invention does not require a further working by means of a machine tool.

DETAILED DESCRIPTION OF THE PREFERRED EMBODIMENTS

This invention will now be described in detail with reference to the following Examples but they should not be construed to be limiting the scope of the present invention.

EXAMPLE 1

An oxygen sensor device as shown in FIG. 12 is used. In the oxygen sensor device, solid electrolyte plate 1 is made of zirconium powder containing 8 mol % of $Y_2O_3$ and has a round shape of a size of 6 mm in diameter and 0.2 mm in thickness. Solid electrolyte plate 1 has, at its center portion, gas inlet means 7 in the form of a through-hole having a diameter of 10 $\mu$m. Two electrodes 2A and 2B are made of platinum and have a size of 4 mm in diameter and 5 $\mu$m in thickness. The entire space of the diffusion chamber defined by glass dome 4 and solid electrolyte plate 1 is filled with porous inorganic material layer 3A which has been prepared by sintering alumina powder having a particle size of not larger than 20 $\mu$m. The thicknesses of the diffusion chamber and the glass dome each are 10 $\mu$m. Electric lead means 6A and 6B respectively connected to electrodes 2A and 2B are formed on upper side surface 15A of leg member 15 by printing a platinum-containing pasty material, followed by sintering. The length of leg member 15 is 22 mm. Electric lead means 9A and 9B connected to heater means 9 is formed on lower side surface 15B of substrate plate 15.

This oxygen sensor device is produced as follows, in accordance with Method (II).

The solid electrolyte plate is prepared as follows. A powder of zirconium containing 8 mol % of $Y_2O_3$ is charged in a rubber tube of an inner diameter of 6 mm. In this instance, a yarn having a diameter of about 10 $\mu$m extends under tension through the axis of the rubber tube. Then, the powder in the rubber tube is compressed and fired at about 1600° C. for 3 hours to obtain a cylindrical solid rod having an aperture extending through the axis thereof and having a diameter of about 10 $\mu$m. The solid rod is sliced in a perpendicular direction to the longitudinal aperture to obtain the solid electrolyte plate having an aperture.

Then, on both surfaces of the electrolyte plate, a platinum-containing pasty material obtained by mixing a platinum powder having a particle diameter of 0.1 to 0.5 $\mu$m with $\alpha$-terpineol is coated by screen printing and sintered to form electrodes. Next, an alumina-containing pasty material obtained by mixing alumina having a particle diameter of not larger than 20 $\mu$m with a mixture of butylcarbitol acetate and nitrocellulose is coated by screen printing over one of the electrodes. The coated alumina-containing layer is dried and sintered at about 1000° C. Over the resultant alumina layer, a pasty material obtained by mixing a mixture of butylcarbitol acetate and nitrocellulose with a glass composed of 12 w/w% of BaO, 15 w/w% of SiO$_2$, 25 w/w% of B$_2$O$_3$, 25 w/w% of MgO and 20 w/w% of ZnO and having a thermal expansion coefficient of $100 \times 10^7/°$ C., is coated by screen printing, followed by firing at 900° C. The outer surface of the glass dome of the resultant composite member is bonded to leg member 15 (having couples each of two electric lead means) by means of an adhesive, to thereby obtain an assembly of the glass dome, the solid electrolyte plate having the first and second electrodes and the leg member attached to the solid electrolyte plate and having the couples each of two electric lead means.

Figure 15B:
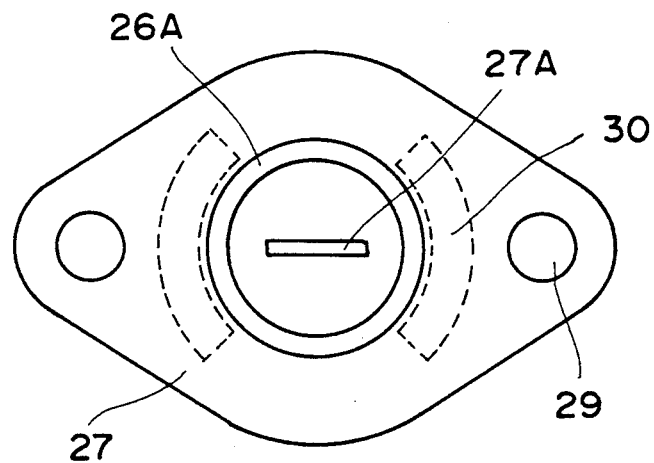
FIG. 15(B) is a diagrammatic plan view of the support plate shown in FIG. 15(A)

As shown in FIG. 15(A) and FIG. 15(B), leg member 15 of the above-obtained assembly together with the couples of electric lead means is fluid-tightly, fixedly inserted in slit 27A of support plate 27 made of alumina. The ceramic support plate 27 has a width of 26 mm, a length of 40 mm and a thickness of 4 mm. The assembly fixed on support plate 27 is covered with cylindrical, gas permeable cap 26 made of alumina and having a diameter of 18 mm. The gas permeable cap is fluid-tightly fixed at its circumferential base edge to groove 26A of support plate 27, to thereby obtain an oxygen sensor device (Device I).

Figure 16:
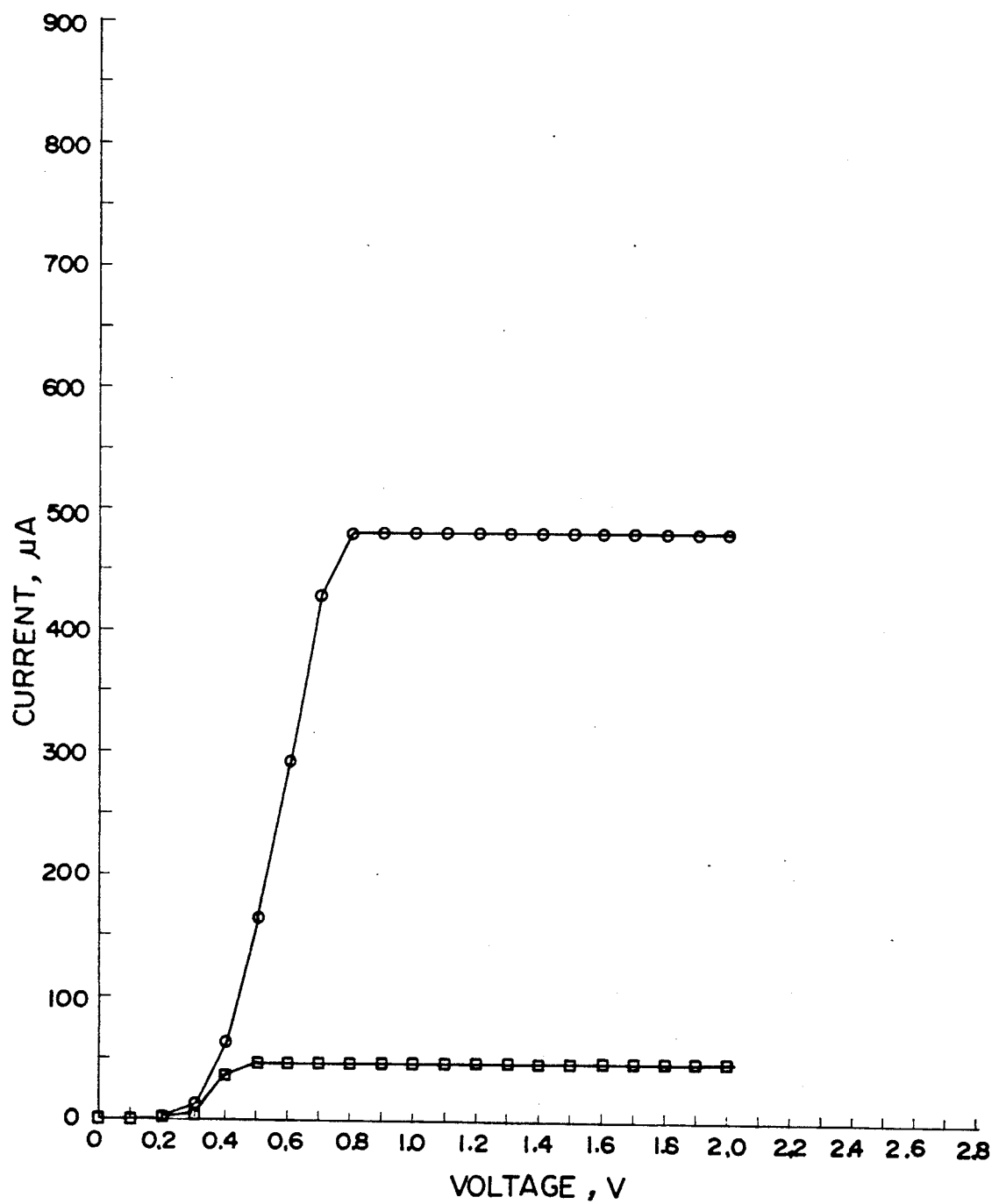
FIG. 16 is a graph showing volt-ampere characteristics exhibited by an oxygen sensor device of the present invention.

An electric current is flowed through heater means 9 of the assembly at a voltage of 3W so that the temperature of the oxygen sensor device is increased to about 450° C. Then, under an atmosphere of a gas containing 21 v/v% oxygen, an electric voltage is applied between two electrodes 2A and 2B and elevated gradually from 0.1 to 2.0V, while measuring the electric current (μA) flowing between the two electrodes. The relationship between the applied electric pressure and the measured electric current is shown in FIG. 16 (see line represented by

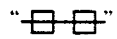

).

Substantially same procedure as mentioned above is repeated except that the oxygen concentration is changed to 90.5 v/v%. The relationship between the applied electric voltage and the electric current measured under the atmosphere of a gas containing 90.5% oxygen is also shown in FIG. 16 (see line represented by

).

Moreover, substantially the same procedure as mentioned above is repeated except that the oxygen concentration is changed as shown in Table 2, to determine a limited current. From the obtained limited current, the oxygen concentration (found) is calculated by the following formula:

$$\text{Oxygen concentration (found)}(\%) = \left\{1 - \exp\left(-\frac{a}{c}\right)\right\} \times 100$$

wherein a is the value of the limited current (μA) and c is a constant (225.1). The results are shown in Table 2.

TABLE 2

| | | | | | | |
|---|---|---|---|---|---|---|
| Oxygen concentration (actual) (v/v %) | 0 | 9.67 | 20.38 | 49.4 | 70.4 | 94.9 |
| Limited current (μA) | 0 | 22.97 | 51.30 | 153.6 | 276.3 | 669.4 |
| Oxygen concentration (found) (v/v %) | 0 | 9.70 | 20.38 | 49.46 | 70.69 | 94.89 |

As apparent from Table 2, the oxygen concentration measured by the oxygen sensor device of the present invention is well in agreement with the actual oxygen concentration of the ambient gas.

Further, using the above-obtained oxygen sensor device, a response to the change in the oxygen concentration of ambient gas is determined as follows.

The oxygen concentration of ambient gas is changed as shown in Table 3. According to the change of the oxygen concentration, the electric current measured by means of the oxygen sensor device is changed. The time required before the oxygen sensor device indicates the occurrence of the 90% change of electric current relative to the entire change (100%) of electric current which entire change corresponds to the change of the limited current, is determined (T$_{90}$, expressed by seconds). The results are shown in Table 3.

TABLE 3

| Change in oxygen concentration (%) | T$_{90}$ (seconds) |
|---|---|
| 21 → 0 | 21 |
| 0 → 21 | 19 |
| 21 → 10 | 9 |
| 10 → 21 | 7 |

As apparent from Table 3, the oxygen sensor device of the present invention shows relatively prompt response to the change in the oxygen concentration of the ambient gas.

Furthermore, the heating and cooling of the oxygen sensor device is repeated 10,000 times to give a heat shock to the sensor device. Then, the resultant sensor device is subjected to examination as mentioned above. As a result, it is found that the properties of the sensor device of the present invention are not changed even after subjected to the repeated heat shock.

EXAMPLES 2 TO 5

(1) An oxygen sensor similar to that shown in FIG. 13 except that gas inlet means 7 is not provided in solid electrolyte plate 1 but provided in glass dome 4 and that through-hole 18 is not provided in leg member 15 is prepared as follows. The formation of electrodes 2A and 2B and porous inorganic material layer 3A on solid electrolyte plate 1 is conducted in the same manner as in Example 1. Then, glass dome 4 is formed on porous inorganic material layer 3A in substantially the same manner as in Example 1 except that immediately after the formation of the glass dome by firing the glass-containing layer at 900° C., cold air is blown to the surface of the glass dome. Thus, an assembly having cracks in the glass dome is obtained. The resultant member is attached to leg member 15 in substantially the same manner as in Example 1 except that the outer surface of solid electrolyte plate 1 is attached to the upper surface of leg member 15 as shown in FIG. 13. The assembly is fluid-tightly, fixedly inserted in slit 27A of support plate 27 and covered with gas permeable cap 26 as in Example 1 to thereby obtain an oxygen sensor device (Device II).

(2) Substantially the same procedure as described above is repeated except that after coating a glass-containing pasty material over the alumina-containing layer, a glass capillary is planted in the center portion of the glass-containing layer. The glass capillary has an inner diameter of 0.2 mm and a length of 2 mm. Then, firing is conducted to form a glass dome. Thus, an assembly having an orifice in the glass dome in the form of a capillary is obtained. The assembly is fluid-tightly, fixedly inserted in slit 27A of support plate 27 and covered with gas permeable cap 26 as in Example 1 to thereby obtain an oxygen sensor device (Device III).

(3) Substantially the same procedure as described in above item (1) is repeated except that after coating a glass-containing pasty material over the alumina-containing layer, a microsphere of a mixture of a glass-containing pasty material and 0.2 w/w% of sodium nitrite ($NaNO_2$) is taken on the tip end of the needle and embedded at the center portion of the glass-containing layer, followed by firing to form a glass dome. Thus, an assembly having an orifice in the glass dome is obtained. The assembly is fluid-tightly, fixedly inserted in slit 27A of support plate 27 and covered with gas permeable cap 26 as in Example 1 to thereby obtain an oxygen sensor device (Device IV).

(4) Substantially the same procedure as described in above item (1) is repeated except that after coating a glass-containing pasty material over the alumina-containing layer, an aluminum string having a diameter of 0.1 mm and a melting point of 700° C. is planted in the center portion of the glass-containing layer so that the planted aluminum string pierces through the glass-containing layer, followed by firing at 700° C. or higher to form a glass dome. The aluminum string planted on the glass-containing layer is melted and diffused into the glass-containing layer during the firing to form an orifice in the glass dome. Thus, an assembly having an orifice in the glass dome is obtained. The assembly is fluid-tightly, fixedly inserted in slit 27A of support plate 27 and covered with gas permeable cap 26 as in Example 1 to thereby obtain an oxygen sensor device (Device V).

With respect to each of device I obtained in Example 1 and devices II to V obtained above, ten sample devices are prepared. Using each of the devices, a limited current under the atmosphere of a gas containing a 1 v/v% of oxygen is determined in the same manner as in Example 1. The results are shown in Table 4. In Table 4, maximum limited current and minimum limited current obtained using ten sample devices with respect to each of devices I to V are shown.

TABLE 4

| Example No. | Device No. | Limited current at 1% $O_2$ (μA) Max. | Min. |
|---|---|---|---|
| 1 | I | 2 | 3 |
| 2 | II | 30 | 60 |
| 3 | III | 130 | 160 |
| 4 | IV | 6 | 80 |
| 5 | V | 70 | 110 |

As apparent from Table 4, devices II to V show relatively large limited current under the atmosphere of a 1% oxygen-containing gas as compared to device A. This means that devices II to V are suitable for use in measuring a relatively low oxygen concentration.

While the invention has been particularly shown and described in reference to preferred embodiments thereof, it will be understood by those skilled in the art that changes in form and details may be made therein without departing from the spirit and scope of the invention.

What is claimed is:

1. An oxygen sensor device comprising:
    an oxygen conductive solid electrolyte plate;
    a first electrode and a second electrode respectively disposed on the upper surface and the lower surface of said solid electrolyte plate;
    a first electric lead means and a second electric lead means for respectively connecting said first and second electrodes to power source means; and
    a glass dome comprising a dome wall directly and fluid-tightly connected at its circumferential base to the upper surface of said solid electrolyte plate to provide a diffusion chamber defined by said dome wall of the glass dome and said solid electrolyte plate, said dome wall of the glass dome comprising at least one glass layer, each layer of said at least one glass layer being dome-shaped and of a single glass composition, said at least one glass layer being directly and fluid-tightly connected at its circumferential base to the upper surface of said solid electrolyte plate;
    at least one of said glass dome and said solid electrolyte plate having a gas inlet means for diffusing ambient gas into said diffusion chamber;
    said glass dome wall having a thermal expansion coefficient in the range of from $70 \times 10^{-7}/°$ C. to $130 \times 10^{-7}/°$ C., said solid electrolyte plate having a thermal expansion coefficient in the range of from $95 \times 10^{-7}$ to $100 \times 10^{-7}/°$ C.;
    said oxygen sensor device being operable by energizing said solid electrolyte plate so that oxygen is pumped out of said diffusion chamber through said solid electrolyte plate to flow electric current across said first and second electrodes, said electric current being indicative of the partial pressure of the oxygen in the ambient gas.

2. An oxygen sensor device according to claim 1, further comprising a porous inorganic material packing layer which is fixedly disposed in the entire space of said diffusion chamber.

3. An oxygen sensor device according to claim 1, further comprising a porous inorganic material semi-packing layer which is fixedly disposed in an upper portion of said diffusion chamber which upper portion is remote from the solid electrolyte plate, while leaving devoid of said porous inorganic material the remainder of said diffusion chamber.

4. An oxygen sensor device according to any one of claims 1, 2 and 3, wherein said gas inlet means is provided in said glass dome.

5. An oxygen sensor device according to any one of claims 1, 2 and 3, wherein said gas inlet means is provided in said solid electrolyte plate.

6. An oxygen sensor device according to claim 5, wherein said gas inlet means is an aperture running through said solid electrolyte plate from one surface thereof to the other surface thereof 7. An oxygen sensor device according to claim 1, further comprising a heater means having a third electric lead means and a fourth electric lead means respectively for connecting said heater means to power source means.

8. An oxygen sensor device according to claim 7, wherein said heater means is disposed on the outer wall surface of said glass dome.

9. An oxygen sensor device according to claim 7, wherein said heater means is disposed on the inner wall surface of the glass dome.

10. An oxygen sensor device according to claim 9, further comprising an electrically insulating porous glass layer provided between the heater means and said first electrode disposed on the upper surface of said solid electrolyte plate.

11. An oxygen sensor device according to claim 7, further comprising an electrically insulating leg member attached at its one end portion to the outer surface of said glass dome or the outer surface of said solid electrolyte plate through an adhesive layer, while leaving unattached a remaining elongate portion and wherein a couple of said first and second electric lead means and a couple of said third and fourth electric lead means each extend on and along the unattached elongate portion of said leg member, wherein said gas inlet means and said leg member satisfy a positional relationship such that a passage is provided for diffusing ambient gas into said diffusion chamber through said gas inlet means and wherein said adhesive layer is non-porous or porous in accordance with the position of said gas inlet means relative to said leg member so that a passage is provided for passing the oxygen pumped out of said diffusion chamber through said solid electrolyte to ambient atmosphere.

12. An oxygen sensor device according to claim 11, wherein said solid electrolyte plate has an aperture as said gas inlet means.

13. An oxygen sensor device according to claim 12, wherein the leg member is attached to the outer surface of said glass dome remote from said aperture of the solid electrolyte plate through said adhesive layer.

14. An oxygen sensor device according to claim 12, wherein said leg member is attached to the outer surface of said solid electrolyte plate through said adhesive layer, and said adhesive layer is porous.

15. An oxygen sensor device according to claim 14, wherein each of said leg member and said adhesive layer has a through-hole in registry with said aperture of said solid electrolyte plate and said adhesive layer is porous.

16. An oxygen sensor device according to any on of claims 11 to 15, further comprising a gas permeable cap and a support plate having a slit and wherein the unattached elongate portion of said leg member is fluid-tightly, fixedly inserted in said slit together with both said couples of electric lead means so that a predetermined length of said elongate portion is protruded, together with the corresponding lengths of both said couples of electric lead means, through said slit of the support plate and wherein said gas permeable cap covers an assembly of said glass dome, said solid electrolyte plate having the first and second electrodes and a portion of said leg member with the corresponding lengths of both said couples of electric lead means, which assembly is positioned above the support plate on the side of said gas permeable cap, leaving a space between said gas permeable cap and said assembly, said gas permeable cap being fluid-tightly fixed at its circumferential base edge to the upper surface of said support plate, said protruded elongate portion of said leg member being adapted to be connected to a connector means of said power source means.

17. An oxygen sensor device according to claim 1, wherein a portion of at least one of said first electrode and said second electrode protrudes outside the glass dome.

* * * * *